United States Patent [19]

Schnabl et al.

[11] Patent Number: 4,720,453
[45] Date of Patent: Jan. 19, 1988

[54] DETECTING ENVIRONMENTAL POLLUTANTS WITH PROTOPLASTS IN ALGINATE MATRIX

[75] Inventors: Heide Schnabl, Ottobrunn; Ulrich Zimmermann, Würzburg; Gottfried Küppers, Heinsberg, all of Fed. Rep. of Germany

[73] Assignee: Kernforschungsanlage Julich GmbH, Julich, Fed. Rep. of Germany

[21] Appl. No.: 633,872

[22] Filed: Jul. 24, 1984

[30] Foreign Application Priority Data

Aug. 1, 1983 [DE] Fed. Rep. of Germany ....... 3327691

[51] Int. Cl.$^4$ ............................................. G01N 33/18
[52] U.S. Cl. ........................................ 435/4; 422/57; 436/34; 436/39; 436/63; 436/82; 436/141
[58] Field of Search ...................... 436/141, 63, 82, 34, 436/39; 435/29, 182, 4, 6; 422/57

[56] References Cited

FOREIGN PATENT DOCUMENTS 0070023 1/1983 European Pat. Off. ............ 435/182
0916373 1/1963 United Kingdom .................. 435/29

OTHER PUBLICATIONS

Chemical Abstracts, I, 94:162739r (1981).
Chemical Abstracts, II, 99:119537q (1983).
Siegel, "Water Air Soil Pollut., 8(3), 1977, pp. 293–304 (Abstract).
Misaghi, *Physiology and Biochemistry of Plant-Pathogen Interactions,* Plenum Press, N.Y. (1982), pp. 86–87.

*Primary Examiner*—Sidney Marantz
*Attorney, Agent, or Firm*—Frishauf, Holtz, Goodman & Woodward

[57] ABSTRACT

Plant protoplasts are suspended in a solution of sodium alginate which is thereafter thickened by the addition of a soluble calcium or lanthanum salt to produce a matrix with large pores permeable to water and gas in which the protoplasts are held. The resulting material, in tape or spheroid form, when stored in a nutrient solution, will prolong the senescence of the protoplasts and increase their sensitivity to polluting materials. When such ribbons or particles are exposed to a polluting environment for a particular period of time, the effect of pollution can be detected by measuring the evolution of ethane or measuring the blocking of the enzyme ribulose-diphosphate-carboxylase, in the latter case using carbon dioxide marked with $^{14}C$. A control experiment in which an identical indicator treated in an equivalent environment without pollutants reveals, by comparison, the effect of the pollution.

11 Claims, No Drawings

DETECTING ENVIRONMENTAL POLLUTANTS WITH PROTOPLASTS IN ALGINATE MATRIX

This invention relates to a method of detecting environmental pollutants by determining the effects of the pollutants on plant cells and with the provision of an indicator utilizing this effect for making the presence of noxious materials evident.

It is known to determine the concentration of pollutants by means of physical analysis methods. The results of such methods, however, do not permit direct conclusions regarding the biological effect of pollutants, because the effect of the pollutants depend not only on the concentration, but also on the combination of the individual pollutants in the environment and thus depends upon the sample to be investigated. Since, in addition, the composition of the polluting materials in environmental samples is in general very complex and the analyses must be limited to the determination of a few important pollutants, no adequate conclusions regarding the biological effect in given environmental conditions can be made and practiced with reference to such analysis results.

It is also known that living cells react to a change in the environmental conditions with a modification of biochemical-physiological processes. Thus, for example, the evolution of ethane indicates physical destruction of the cell membrane. Biochemicalbiophysical experiments are also known according to which these effects can be detected with the use of entire plants or by means of leaf segments which have been exposed to pollutants. In contrast to intact plants, plant protoplasts are much more sensitive to toxic substances. They have only a short lifetime and are only available for brief periods.

SUMMARY OF THE INVENTION

It is an object of this invention to provide a sensitive determination of the effects of pollutants proceeding on the basis of plant cells, with test samples of wall-less cells that are operable over longer periods and can be made available as identical test cell samples.

Briefly, protoplasts, the living portions of plant cells, also known as energids, are immobilized in order to prolong their senescence, in a matrix through which gas and water may pass. The thus immobilized protoplasts are exposed for a time in a medium containing the pollutants, after which the intensity of the changed biochemical-physiological processes resulting from the effect of the pollutants is determined. There can be used as protoplasts for this purpose, for example, protoplasts from monocotyledonous or dicotyledonous plants and also yeast cells.

The immobilization of protoplasts takes place conveniently in a calcium alginate matrix or in a lanthanum alginate matrix. The alginate matrix consists of over 90% water and has large pores. In that way it is possible on the one hand for the nutrient solution to reach the protoplasts without hindrance and, on the other hand, the contact of the polluting materials with the protoplasts is in no way limited. Furthermore, it has been found that the sensitivity of the protoplasts to the pollutants is substantially reinforced with the increase of age, so that a rise in cell sensitivity is obtained.

By the immobilization itself and suitable storage which can usefully take place at a temperature in the region from 2° to 6° C., a holding time of 10 to 14 days can be obtained for protoplasts immobilized in calcium alginate and storage in useful condition of up to three months can be obtained for protoplasts immobilized in lanthanum alginate. Protoplasts in suspension, in contrast to the foregoing, are capable of being usefully stored for only a few hours.

The effect of the pollutants on the protoplasts can be determined, for example, by the amount of blocking of ribulose-1,5-diphosphatecarboxylase, the most important enzyme for the photosynthesis (fixation of $CO_2$) process. That is radiochemically determined by the pickup of $14_{CO_2}$.

A particularly advantageous variant of the process of the invention consists in determining the rate of emission of ethane out of the protoplasts. Ethane is generated as the product of the peroxidation of unsaturated fatty acids which are bound to the cell membrane and when so generated it can be simply and very quickly measured by gas chromotography. Extensive measurements have shown, moreover, that the formation of ethane is proportional to the pollutant concentration.

The process of the invention makes use of a novel indicator which is distinguished by having plant protoplasts stored or held in a matrix that is highly permeable to gas and water. A calcium alginate matrix and preferably a lanthanum alginate matrix, is suitable for the matrix, as above noted. Of couse other matrices can be used which permit, on the one hand, a nutrient solution and, on the other hand, also the pollutants to reach the protoplasts.

The indicator, as used, then can have various shapes and sizes. It has been found advantageous and handy for the indicator to be provided in small spheroids, of a diameter between about 1 mm and about 5 mm. The indicator can also be provided in band or tape form with a thickness of about 1 to 2 mm.

The procedure for making an indicator according to the invention can be as follows:

A portion of a freshly produced protoplast suspension is stirred into a 3 to 6% (according to the cell type) isotonic sodium alginate solution and then enmeshed, according to the matrix desired, with $Ca^{2+}$ or $La^{3+}$ ions.

For making the indicator in tape or ribbon form, the protoplast suspension in sodium alginate is allowed to run out in stripes and only thereafter is it firmed by the addition of the above-mentioned ions.

For making a spherical indicator, the alginate solution containing the protoplast suspension can conveniently be allowed to drop into the thickening solution (10 mM $CaCl_2$ or preferably 10 mM $La(NO_3)_3$ in isotonic mannitol solution). In practice the indicator is then stored in a nutrient solution with addition of antibiotics (penicillin, streptomycin).

EXAMPLE 1

A 7-day old ribbon-shaped indicator was used having a length of about 5 cm, a width of about 1 cm and a thickness of about 2 to 3 mm which contained immobilized Vicia-Faba protoplasts. The indicator was put for 30 minutes in a solution that contained 0.5M (molar) of mannitol as osmotic control agent and 14 micromol of pentachlorphenol (PCP) as pollutant. The indicator was immediately thereafter exposed to light (200 W/cm$^2$) in a Fernbach flask for one hour at 22° C. Then a 1 mL gas sample was taken from the flask and analyzed for ethane by gas chromatography. The ethane production per unit of time could thus be determined.

A measure for the number of cells exposed was the chlorophyll content of the indicator used.

The determination of ethane gave the result of 135 pmols of ethane per milligram of chlorophyll per hour.

A control measurement with the same indicator which was not exposed to the pollutant gave the result of 60 pmols of ethane per milligram of chlorophyll per hour.

EXAMPLE 2

Measurements were carried out in accordance with Example 1 with an indicator containing Avena-Sativa protoplasts. The measurement result was 150 pmols of ethane per milligram of chlorophyll hour.

The control measurement was 65 pmols of ethane per milligram of chlorophyll per hour.

EXAMPLE 3

An indicator corresponding to Example 1 was used. This was put for 30 minutes in a 0.5M (molar) mannitol solution which also contained 220 μmol $HgCl_2$ as pollutant. After unbedding of the protoplasts from the matrix with citrate buffer (20 mM; pH 7.6; in 0.8M mannitol) the activity of the enzyme ribulose-1.5-diphosphatecarboxylase was determined by the pickup of $^{14}C$. The protoplasts for that purpose were put into 0.5 mL of a solution which contained 0.1M tris-HCl-buffer (pH=8.3), 5 mM dithiothreitol, 10 mM $MgCl_2$, 50 mM Nah $^{14}CO_3$ (specific activy $7.2.10^5$ Bq $\mu\text{-mol}^{-1}$), 1 mM ribulose diphosphate, as well as 0.8M mannitol. They were irradiated for 30 minutes with a light intensity of 15,000 1×. Immediately thereafter the solution was removed and stopped down with methanol (75%) in a volume ratio of 1:1. The $^{14}CO_2$ pickup was then determined by means of a liquid scintillation counter. The $^{14}CO_2$ pickup in $\mu$-mol per mg of chlorophyll (Chl) per hour was selected as a measure for the enzyme activity.

Result of the measurement: 100 μmol $^{14}CO^2$ (mg $(ch7)^{-1}h^{-1}$).

Control sample (without pollutant): 1750 μmol $^{14}CO_2$ (mg ch7)$^{-1}h^{-1}$).

We claim:

1. Method of detecting environmental pollutants by determining noxious effect of a fluid environment on plant cell protoplasts comprising the steps of:
    enhancing the sensitivity of protoplasts of plant origin to pollution and prolonging the senescence period of said protoplasts in a fibrous matrix of mesh sufficiently large to allow gas or waster to pass through said matrix and to have access to protoplasts immobilized therein, by:
        suspending said protoplasts in an isotonic solution of a soluble alginable; and
        bringing the alginate solution, in which said protoplasts are suspended, into contact with a solution containing ions of at least one metal selected from the group consisting of calcium and lanthanum to produce an alginate matrix holding said protoplasts therein;
    exposing protoplasts immobilized in said matrix to contact with a fluid medium containing at least one material having a noxious effect on living plant matter; and
    measuring intensity of at least one biochemical-physiological process of the exposed protoplasts subject to change by the noxious effects of pollutants, and comparing the process intensity measurement with a corresponding process intensity in the absence of pollution.

2. Method according to claim 1, in which said ions are calcium ions and the matrix produced is a calcium alginate matrix.

3. Method according to claim 1, in which said ions are lanthanum ions and the matrix produced is a lanthanum alginate matrix.

4. Method according to claim 1, in which after said alginate matrix containing protoplasts is produced, the protoplasts immobilized in said matrix, along with said matrix, are stored in a nutrient solution at a temerature in the range from 2° to 6° C.

5. Method according to claim 1, in which said process intensity measurig step is a step of determining the blocking of the effect of ribulose-1.5-diphosphate-carboxylase to promote a so-called photosynthesis reaction in which chlorophyll participates, which effect ribulose-1.5-diphosphate carboxylase is known to be capable of promoting.

6. Method according to claim 1, in which said process intensity measuring step is a determination of the rate of evolution of ethane out of the protoplasts.

7. Indicator material for detecting pollutants comprising protoplasts of plant origin enmeshed in a fibrous lanthanum alginate matrix of small enough mesh to immobilize said protoplasts and of great enough mesh to allow passage of gas and water through said matrix, said indicator being ready for use by virtue of having been kept in contact with a nutrient solution from the time of making until the time of using.

8. Indicator material according to claim 7, in which said matrix containing said protopasts is put into the shape of spheroids.

9. Indicator material according to claim 8, in which the diameter of said spheroids is in the region from 1 to 5 mm.

10. Indicator material according to claim 7, in which said matrix containing said protoplasts is made in ribbon shape.

11. Indicator material according to claim 10, in which the thickness of said ribbon-shaped matrix containing protoplasts is in the range from 1 to 2 mm.

* * * * *